United States Patent [19]

Price

[11] Patent Number: 5,344,920

[45] Date of Patent: Sep. 6, 1994

[54] METHOD OF SEPARATING GLYCOSYLATED AND NON-GLYCOSYLATED PROLACTIN BY ION EXCHANGE CHROMATOGRAPHY

[75] Inventor: Albert E. Price, Marlborough, Mass.

[73] Assignee: Genzyme Corporation, Cambridge, Mass.

[21] Appl. No.: 57,587

[22] Filed: May 4, 1993

[51] Int. Cl.$^5$ .................... A23J 1/00; A61K 37/24
[52] U.S. Cl. ........................ 530/416; 530/399
[58] Field of Search .................... 530/417, 399, 416; 514/2

[56] References Cited

PUBLICATIONS

Kacsoh et al., Endocrine Regulations, vol. 25, 98–110, 1991.
Lewis et al., Endocrinology, vol. 116, No. 1, pp. 359–363, 1985.
Young et al., Mol. & Cellular Endocrinology, 71 (155–162), 1990.
Chapitis et al., Am. J. Obstet. Gynecol., Apr. 1988, vol. 158, No. 4, pp. 846–853.
Pharmacia Fine Chemicals Booklet, Mar. 1980, pp. 32–38.

*Primary Examiner*—David M. Naff
*Assistant Examiner*—Michael V. Meller
*Attorney, Agent, or Firm*—William G. Gosz; F. Brad Salcedo

[57] ABSTRACT

This invention relates to a method for separating glycosylated prolactin from non-glycosylated prolactin. The method comprises the following steps: 1) equilibrating the prolactin containing solution with an equilibrating solution containing at least one organic solvent; 2) adding the equilibrated prolactin solution onto a chromatographic column containing a packing for the ion-exchange affinity separation of glycosylated and non-glycosylated prolactin; 3) eluting the glycosylated prolactin from the chromatographic column with a sufficient quantity of a first eluting solution containing at least one organic solvent and with or without at least one salt, wherein the salt concentration and/or organic solvent concentration and/or pH are appropriate for the eluting of glycosylated prolactin being substantially free of non-glycosylated prolactin; and 4) eluting the non-glycosylated prolactin from the chromatographic column with a sufficient quantity of a first eluting solution containing at least one organic solvent and with or without at least one salt, wherein the salt concentration and/or organic solvent concentration and/or pH are appropriate for the eluting of non-glycosylated prolactin being substantially free of glycosylated prolactin.

21 Claims, No Drawings

METHOD OF SEPARATING GLYCOSYLATED AND NON-GLYCOSYLATED PROLACTIN BY ION EXCHANGE CHROMATOGRAPHY

BACKGROUND OF THE INVENTION

Prolactin is a peptide hormone of 199 amino acids which is produced by the anterior pituitary gland. This hormone has a variety of biological activities in mammals, including lactogenesis and modulation of the immune system. Receptors for prolactin have been found on over fifty different cell types. A number of variants of the hormone have been identified. These include post-translational modifications such as glycosylation, phosphorylation, disulfide dimerization and proteolytic cleavages, as well as alternatively spliced forms. The biological role of these variants is not fully understood. It is postulated that different variants of the molecule may be responsible for the diverse physiological actions of prolactin. In humans, the primary form in the pituitary gland is non-glycosylated, while the glycosylated form predominates in circulation.

The method most commonly used to separate glycosylated prolactin from non-glycosylated prolactin is lectin affinity chromatography. This technique is used in the purification of prolactin from many sources. These include: glycosylated human prolactin from pituitary explants (Lewis et al. *Endocrinology,* 124: 1558-1563, 1989), glycosylated ovine prolactin from pituitary explants (Lewis et al., *Proc. Natl. Acad. Sci.,* 81: 203-215, 1991), glycosylated porcine prolactin from pituitary explants (Sinha et al., *Mol. Cell. Endocrinology,* 80: 203-215, 1988) and human glycosylated prolactin from cultured prolactinoma cells (Pellegrini et al., *Endocrinology,* 122: 2667-2674, 1988). The most commonly used lectins are Concanavalin A (Con A) and lens culinaris (lentil).

The use of reverse phase chromatography in the separation of glycosylated and non-glycosylated prolactin has also been reported. See Noso et al., *Int. J. Peptide Protein Res.,* 39: 250-257, 1992.

The lectin chromatography method of prolactin purification presents binding specificity problems. Both naturally occurring and recombinant glycoproteins will often be produced with a heterogenous range of attached oligosaccharide chains. Due to their binding specificity, a given lectin may not bind all of the oligosaccharide forms present. In fact, a number of investigators have reported working with forms of naturally-derived glycosylated prolactin which will not bind to the particular lectin being used for purification.

The low efficiency of lectin affinity chromatography makes it a poor choice for preparative scale processes. Lectin affinity resins typically have a low binding capacity. This makes purification processes cumbersome and may also lead to the contamination of non-glycosylated fractions with glycosylated prolactin. In addition, lectin resins are not typically available on rigid matrixes which will support the high flow rates which are desirable for production scale purification. A further complicating factor is that the lectin proteins can leach off the column during purification. Further purification steps may be needed since lectins are often highly toxic and would complicate in vivo studies.

Reverse phase chromatography also presents drawbacks in the separation of glycosylated and non-glycosylated proteins since it relies upon the use of high concentrations of acetonitrile and may also utilize strong acids such as trifluoroacetic acid (TFA). The use of these solvents and acids may have an adverse effect upon protein function.

SUMMARY OF THE INVENTION

This invention relates to a method for separating glycosylated prolactin from non-glycosylated prolactin. The method comprises the following steps: 1) equilibrating the prolactin containing solution with an equilibrating solution containing at least one organic solvent; 2) adding the equilibrated prolactin solution onto a chromatographic column containing a packing for the ion-exchange affinity separation of glycosylated and non-glycosylated prolactin; 3) eluting the glycosylated prolactin from the chromatographic column with a sufficient quantity of a first eluting solution comprising at least one organic solvent and at least one salt, wherein the salt concentration, organic solvent concentration and pH are appropriate for the eluting of glycosylated prolactin being substantially free of non-glycosylated prolactin; and 4) eluting the non-glycosylated prolactin from the chromatographic column with a sufficient quantity of a first eluting solution comprising at least one organic solvent and at least one salt, wherein the salt concentration, organic solvent concentration and pH are appropriate for the eluting of non-glycosylated prolactin being substantially free of glycosylated prolactin.

In the alternative, the method comprises a method as described above except that step 4 occurs before step 3, as a result, the non-glycosylated prolactin is eluted prior to the glycosylated prolactin.

Further in the alternative, the method comprises a method as described above except that in step 3, the first eluting solution comprises at least one organic solvent, wherein the organic solvent concentration and pH are appropriate for the eluting of glycosylated prolactin being substantially free of non-glycosylated prolactin.

The present invention, further relates to a method as described above except that in step 4, the second eluting solution comprises at least one organic solvent, wherein the organic solvent concentration and pH are appropriate for the eluting of non-glycosylated prolactin being substantially free of glycosylated prolactin.

In contrast to the methods that are currently employed, the present invention permits the separation of the above mentioned forms of prolactin while maintaining high column loading capacity and high flow rates. The method of the present invention is fully scaleable.

DETAILED DESCRIPTION OF THE INVENTION

This invention is based upon the discovery that large quantities of glycosylated prolactin can be separated from non-glycosylated prolactin by a one step ion exchange chromatographic process utilizing a solution containing low concentrations (i.e., concentrations below 50%) of at least one organic solvent. The single column process can yield glycosylated prolactin of purity greater than 95% range and non-glycosylated prolactin of purity over 99%.

The method of the present invention is useful in separating glycosylated and non-glycosylated prolactin from various sources. They include prolactin samples (i.e., prolactin containing both glycosylated and non-glycosylated forms) derived from human, ovine and porcine pituitary explants. In addition prolactin produced by recombinant cells and cultured prolactinoma cells can also be used in the method of the present invention.

The first step in the method of the present invention begins with equilibrating the sample solution (i.e., containing prolactin) with an equilibrating solution, a solution containing at least one organic solvent. Any standard dialysis method which allows for the equilibration of two different solutions is suitable for use in the present method. For example, a prolactin solution can be placed into dialysis tubing and allowed to equilibrate or dialyze in a solution containing an organic solvent over a sufficient period of time to allow for equilibration.

The equilibrating solution of the present invention consists of a solution containing at least one organic solvent, preferably at low concentrations (i.e., concentrations below 50%). For example, a suitable equilibrating solution may consist of 25% ethylene glycol and 5% n-butanol.

Any standard chromatographic column is suitable in the method of the present invention, such as ones constructed of plastic, glass or stainless steel.

Suitable packing for the chromatographic column includes any beaded agarose (i.e., complex polysaccharide) matrix, such as the synthetic ion exchange resin Sepharose ® (Pharmacia, Piscataway, N.J.). However, any standard packing for the ion exchange separation of proteins may be suitable. See Scopes, R., *Protein Purification: Principles and Practice,* Springer-Verlag, 1982.

The eluting solutions (i.e., the first and second eluting solutions) of the present invention are standard chromatographic solutions, i.e., solutions used to elute proteins from ion exchange chromatographic packing (see Scopes, 1982), with the additional element of containing at least one organic solvent. Suitable organic solvents include alcohols and glycols or mixtures thereof, preferably lower alcohols and glycols, i.e., C1 to C4 alcohols and glycols. In a preferred embodiment, these solutions contain ethylene glycol and n-butanol.

The first eluting solution has either a salt concentration, organic solvent concentration and pH, or an organic solvent concentration and pH that is suitable for eluting a sample from the chromatographic column that is substantially glycosylated prolactin and substantially free of non-glycosylated prolactin. For example, a suitable first eluting solution is a 300 mM NaCl, pH 5, 5% ethylene glycol and 5% n-butanol solution. Sample yields of a purity of greater than 95% glycosylated prolactin have been achieved using the above-mentioned first eluting solution.

The second eluting solution has a salt concentration, organic solvent concentration and pH, or an organic solvent concentration and pH that is suitable for eluting a sample from the column that is substantially non-glycosylated prolactin and substantially free of glycosylated prolactin. For example, a suitable second eluting solution is a 25 mM tricine, pH 8.5, 5% ethylene glycol and 5% n-butanol solution. Sample yields of a purity of greater than 99% non-glycosylated prolactin have been achieved using the above-mentioned second eluting solution.

The invention will be further illustrated by the following non-limiting Exemplification:

EXEMPLIFICATION

Materials and Methods

Cloning and Expression

The human prolactin (PRL) gene was obtained from ATCC #31721 as a sample of *E. coli*/1776 containing the plasmid pBR322-HumPrl. The PRL cDNA-containing plasmid was isolated and transformed into *E. coli* MC1061. To facilitate expression, the human PRL coding sequence was cloned into pUC18-BabPrl, a vector used for the expression of baboon PRL (Cole, et al., *Endocrinology,* 129: 2639–2646, 1991). The HumPrl plasmid was isolated via miniprep, digested with the restriction enzyme PpuMI, and the 690 bp fragment containing the human PRL coding region was gel isolated. The baboon PRL coding sequence was removed from pUC18-BabPrl by restriction digest with PpuMI and the vector fragment was isolated. The pUC18-BabPrl PpuMI vector fragment and human Prl PpuMI fragment were ligated together and transformed into MC1061 to generate pUC18-humPrl. The humPRl cDNA was then transferred as a 750 bp BamH1 fragment into pCS1 to generate pCS1-humPrl. In pCS1-humPrl the PRL cDNA is flanked by XhoI and SalI restriction sites.

To facilitate expression in mammalian cells the PRL cDNA was cloned as a 750 bp SalI/XhoI fragment from pCS1-humPrl into the unique XhoI restriction site of the bovine papilloma virus based vector CLH3ALXBPBXTNEO. Transcription in the CLH3ALXBPBXTNEO-HumPrl construct is initiated by the murine metallothionein-I promoter and terminated by the simian virus 40 early polyadenylation signal, as described by Hsiung, et al., *J. Mol. Appl. Genet.,* 2: 497–506 (1984) and Reddy et al., *DNA,* 6: 461–472 (1987). Other components of the vector are the bovine papilloma virus genome which allows episomal maintenance of the plasmid in murine C127 cells, the neo gene which confers G418 resistance to mammalian cells, and the pML derivative of pBR322 which permits growth and selection of the plasmid in *E. coli*. A correct clone was identified by minipreps and transformed into another bacterial host, DH-5. A stable clone was isolated and expanded.

The CLH3ALXBPBXTNEO-HumPrl construct was transfected into murine C127 cells by the method of calcium phosphate precipitation. G418-resistant foci were isolated and the conditioned culture supernatants were analyzed by ELISA for secreted PRL. The cell lines with the best PRL secretion rates and growth characteristics were then selected for large scale production.

Tissue Culture

The human PRL-producing cells were cultured for large scale production in suspension culture in 8 liter spinner flasks. The cells were grown and maintained on DE52 microcarriers in a proprietary medium designated 925, and supplemented during growth with 10% donor calf serum. After growth, the cells were maintained in 925 medium without serum and conditioned medium used for the purification of recombinant human PRL was harvested every 24 hours for a period of 21 days.

Assay Methods

Recovery of rh PRL was determined by ELISA. The coating antibody was mouse anti-human PRL monoclonal (Zymed, San Fransico, Calif., catalogue #03-2400, clone 2MPL1). The secondary antibody was an HRP-conjugated mouse anti-human PRL monoclonal (BioDesign International, Kennebunkport, Me., catalogue #E-45631P, clone 6204). Recombinant human prolactin, (Genzyme Corp., Cambridge, Mass., lot 0201), was used as standard at a range of 0–25 ng/mL. Concentration of the standard was determined by amino acid analysis. Colorimetric development was via OPD, and the plates were read in a Molecular Devices VMAX microplate reader.

Protein concentrations were determined using the Pierce BCA Protein assay (Pierce, Rockford, Ill.) BSA as a standard, and by amino acid analysis as described by Cole, et al., 1991.

SDS polyacrylamide gel electrophoresis was performed according to the method of Laemmli (*Nature*, 227: 680–685, 1970) on 10×10 cm 10–20% acrylamide gels obtained from Integrated Separation Systems (Hyde Park, Mass.). Gels were stained with Coomassie blue stain R-250 (Bio-Rad, Richmond, Calif.) and Bio-Rad low mw standards were used for molecular weight comparison. Gel bands were electroblotted onto nitrocellulose and probed with polyclonal rabbit antihuman PRL antisera from Ventrex Corporation (Portland, Me.) for Western blot analysis. Lectin blots were performed using biotinylated lentil lectin (lens culinaris) from Vector Laboratories (Burlingame, Calif.). Laser densitometry of coomassie-stained gels was performed on an LKB 2202 laser densitometer with Maxima data acquisition and peak analysis software (Millipore, Bedford Mass.).

Amino terminal sequence analysis was performed as described by Cole, et al., 1991, using an Applied Biosystems 470 gas phase sequencer.

Monosaccharide analysis was performed as described by Cole et al., 1991, using the Dionex Carbohydrate Analysis System (Sunnyvale, Calif.). Sialic acid content was determined by the thiobarbituric acid method.

Molecular weight was determined by laser desorption mass spectroscopy on a Finnigan MAT 'Laser MAT' mass spectrometer. The PRL samples were mixed 1:1 (v/v) in a sinapinic acid matrix and run at positive polarity with accelerating voltage of 20015 volts.

Size exclusion chromatography was performed on a Bio Sil TSK-250 column (600×7.5 mm) in 25 mM MES buffer, pH 6.5, 100 mM NaCl. Retention times were regressed against those for individual mw standards: cytochrome C, chymotrypsinogen A, hen egg albumin, bovine serum albumin, and aldolase.

PRL bioactivity was determined using Nb2 cell (rat lymphoma cells) proliferation assay as described in Tanaka et al., *J Clin Endocrin Metab*, 51:1058–1063 (1980). Nb2 cells were obtained from Dr. Henry Friesen, University of Manitoba, Manitoba Canada.

Protein Purification

Following harvest from spinner flasks, PRL containing media was clarified on 30" serial CRK1 and CWO3 filters (Millipore, Bedford, Mass.) and sterile filtered on 0.2 u Milidisk 200 (Millipore) into autoclaved media vessels. All weekly harvest pools were combined prior to purification.

Conditioned media was diluted 2.6× with water for injection (WFI) to conductivity <4.0 mS/cm, 4° C. pH was adjusted to 5.0 using 3N acetic acid. The media was then loaded onto a 10 liter S Sepharose Fast Flow column (Pharmacia) equilibrated in 50 mM sodium acetate, pH 5.0, 0.01% Tween 80 and column performance was monitored at 280 nM. After washing to baseline, the column was washed with 50 mM sodium acetate, pH 5.0, 90 mM sodium chloride, 0.01% Tween 80. PRL was then eluted from the column with 25 mM HEPES, pH 8.0, 0.01% Tween 80.

S eluate was loaded onto a 1.0 liter Q Sepharose Fast Flow column (Pharmacia) equilibrated in 25 mM HEPES, pH 8.0, 0.01% Tween 80. After washing to baseline, the column was eluted in a gradient of 0–350 mM NaCl, 25 mM HEPES, pH 8.0. Fractions were collected and analyzed for purity by SDS-PAGE/laser densitometry. Fractions were then pooled for maximum purity.

Separation of Glycosylated (G-PRL) from Non-glycosylated Prolactin (NG-PRL)

100 mg of highly purified PRL was dialyzed to 50 mM sodium acetate, pH 5.0, 2 μM pepstatin A, and then adjusted to 25% ethylene glycol/5% n-butanol. This solution was allowed to incubate overnight at 4° C. This PRL containing solution was then loaded onto a 50 mL S Sepharose High Performance column (Pharmacia) equilibrated to 50 mM sodium acetate, pH 5.0, 2 uM, pepstatin A, 5% ethylene glycol/5% n-butanol. After washing to baseline, the column was washed with 50 mM sodium acetate, pH 5.0, 2 uM pepstatin A, 5% ethylene glycol/5% n-butanol, 200 mM sodium chloride. G-PRL was then eluted from the column with 50 mM sodium acetate, pH 5.0, 2 uM Pepstatin A, 5% ethylene glycol/5% n-butanol, 300 mM sodium chloride. A small amount of mixed G-PRL and NG-PRL was then washed from the column with 50 mM sodium acetate, pH 5.0,2 uM pepstatin A, 5% ethylene glycol/5% n-butanol, 1M sodium chloride. Pure NG-PRL was then eluted from the column with 25 mM Tricine, pH 8.5, 5% ethylene glycol/5% n-butanol. Fractions were collected throughout the elution program, analyzed by SDS-PAGE, and pooled for maximum separation of forms.

Enzyme Digestion

Recombinant N-Glycanase enzyme was obtained from Genzyme Corporation (Cambridge, Mass.). 4 μg of G-PRL was desiccated to dryness and reconstituted in 10 μL 10 mM sodium phosphate buffer, pH 7.5, 0.5% SDS, 0.1M 2-mercaptoethanol. The samples were boiled for 5 minutes. 5 μL 10% octylglucoside was added to protect the enzyme from SDS. 5 units recombinant N-Glycanase were added and the mixture was incubated overnight at 37° C.

Results

The two-column purification process described in 'Materials and Methods' yielded a protein mixture consisting of two major bands on coomassie-blue stained gradient gels. These bands had molecular weights judged to be approximately 25 kD and 23 kD, respectively. The proportions of these two bands were judged to be approximately 14% 25 kD form and 86% 23 kD by laser densitometry of these gels. These two bands were identified as human PRL by western blotting with anti-human PRL antisera. The purity of human PRL in this mixture was judged to be >97% by laser densitometry of the PRL-staining bands. Overall recovery of the PRL by ELISA was 53% (see Table 1).

TABLE 1

PRL PURIFICATION RECOVERY

| Step | mg PRL ELISA | % Yield | mg Protein BCA | Mass Fraction | Purity |
|---|---|---|---|---|---|
| media | 2989 | 100 | 9395 | 0.318 | |
| S eluate | 3444 | 115 | 3328 | 1.035 | 91% |
| Q eluate | 1583 | 53 | 1331 | 1.189 | 97% |

The results of N-terminal sequence analysis indicate that no non-PRL sequences are present.

Glycosylated and non-glycosylated forms of PRL were separated on an S Sepharose High Performance column in the presence of 5% ethylene glycol/5% n-butanol, as described in 'Materials and Methods'. The G-PRL obtained from this process was estimated to be 95% G-PRL/5% NG-PRL by laser densitometry of coomassie-stained gels. The NG-PRL obtained from this process was estimated to be >99% NG-PRL by the same method. Overall recovery of PRL in the separation process was 65% by amino acid analysis (aaa) (see Table 2).

TABLE 2

G-PRL & NG-PRL Separation Recovery

| step | mg PRL aaa | % Yield |
|---|---|---|
| SS-HP load | 112 | 100 |
| G-PRL | 9.74 | 65.5* |
| NG-PRL | 63.65 | |

*65.5 refers to the combined G-PRL and NG-PRL.

G-PRL was digested with N-Glycanase and neuraminidase, and the products run on SDS-PAGE. The results of these digests show a clear shift of the 25 kD band down to the 23 kD form, indicating that the 25 kD form is n-glycosylated. The neuraminidase digest also showed a slight downward shift of the 25 kD form, indicating that this form is also silylated.

The result of the N-Glycanase digest was substantiated by lectin blotting of total PRL with lentil lectin. These blots show clear staining of the 25 kD PRL band, with no staining in the 23 kD region, indicating again that the 25 kD band is N-glycosylated. A lectin blot was also performed using isolectin B4 from BS-I lectin, which is specific form alpha 1, 3 terminal galactosyl residues. The clear staining of the 25 kD band strongly suggests that terminal alpha 1, 3 galactosyl residues are present.

N-glycosylation and silylation of our recombinant human PRL was confirmed by monosaccharide and sialic acid analyses of the PRL mixture and of the separated 25 kd and 23 kD forms. The monosaccharide ratios from this analysis suggest that a minimal complex-form oligosaccharide chain is present, that these chains may be fucosylated, and that 40% of the oligosaccharides are silylated.

Molecular weights of recombinant human G-PRL and NG-PRL by laser desorption mass spectroscopy were 25596 daltons and 23671 daltons, respectively.

Biological activity of the gross PRL mixture, as well as that of the separated 25 kD and 23 kD forms was determined using the Nb2 cell proliferation assay described in 'Materials and Methods'. The results of the Nb2 assay utilizing the separated PRL forms indicate: (1) that full biological activity of our recombinant human PRL is maintained after exposure to 5% ethylene glycol/5% n-butanol in the separation process, and (2) that the 23 kD non-glycosylated PRL is 3-5 times more active in this assay than the 25 kD glycosylated PRL.

Equivalents

Those skilled in the art will recognize, or be able to ascertain, using no more than routine experimentation many equivalents to the specific embodiments of the invention described herein. Such equivalents are intended to be encompassed by the following claims:

I claim:

1. A method for separating glycosylated prolactin from non-glycosylated prolactin comprising:
   a. equilibrating a solution containing glycosylated and non-glycosylated prolactin with an equilibrating solution containing at least one lower alcohol and/or lower glycol;
   b. adding the equilibrated prolactin solution onto a chromatographic column containing a cationic or anionic packing for the ion exchange separation of glycosylated and non-glycosylated prolactin;
   c. eluting the glycosylated prolactin from the chromatographic column with a sufficient quantity of a first eluting solution comprising:
      i. at least one lower alcohol and/or lower glycol in concentration less than 50% per total volume; and
      ii. at least one salt, wherein the salt concentration, lower alcohol and/or lower glycol concentration and pH are appropriate for the eluting of glycosylated prolactin being substantially free of non-glycosylated prolactin; and
   d. eluting the non-glycosylated prolactin from the chromatographic column with a sufficient quantity of a second eluting solution comprising:
      i. at least one lower alcohol and/or lower glycol in concentration less than 50% per total volume; and
      ii. at least one salt,
      wherein the salt concentration, lower alcohol and/or lower glycol concentration and pH are appropriate for the eluting of non-glycosylated prolactin being substantially free of glycosylated prolactin.

2. A method according to claim 1, wherein the prolactin is human prolactin.

3. A method according to claim 1, wherein the lower alcohol is n-butanol.

4. A method according to claim 1, wherein the lower glycol is ethylene glycol.

5. A method according to claim 1, wherein the packing is a resin.

6. A method for separating glycosylated prolactin from non-glycosylated prolactin comprising:
   a. equilibrating a solution containing glycosylated and non-glycosylated prolactin with an equilibrating solution containing at least one lower alcohol and/or lower glycol;
   b. adding the equilibrated prolactin solution onto a chromatographic column containing a cationic or anionic packing for the ion exchange separation of glycosylated and non-glycosylated prolactin;
   c. eluting the glycosylated prolactin from the chromatographic column with a sufficient quantity of a first eluting solution comprising:

i. at least one lower alcohol and/or lower glycol in concentration less than 50% per total volume; and ii. at least one salt, wherein the salt concentration, lower alcohol and/or lower glycol concentration and pH are appropriate for the eluting of non-glycosylated prolactin being substantially free of glycosylated prolactin; and d. eluting the glycosylated prolactin from the chromatographic column with a sufficient quantity of a second eluting solution comprising:

i. at least one lower alcohol and/or lower glycol in concentration less than 50% per total volume; and ii. at least one salt, wherein the salt concentration, lower alcohol and/or lower glycol concentration and pH are appropriate for the eluting of glycosylated prolactin being substantially free of non-glycosylated prolactin.

7. A method according to claim 6, wherein the prolactin is human prolactin.

8. A method according to claim 6, wherein the lower alcohol is n-butanol.

9. A method according to claim 6, wherein the lower glycol is ethylene glycol.

10. A method according to claim 6, wherein the packing is a resin.

11. A method for separating glycosylated prolactin from non-glycosylated prolactin comprising:

a. equilibrating a solution containing glycosylated and non-glycosylated prolactin with an equilibrating solution containing at least one lower alcohol and/or lower glycol;

b. adding the equilibrated prolactin solution onto a chromatographic column containing a cationic or anionic packing for the ion exchange separation of glycosylated and non-glycosylated prolactin;

c. eluting the glycosylated prolactin from the chromatographic column with a sufficient quantity of a first eluting solution containing at least one lower alcohol and/or lower glycol in concentration less than 50% per total volume; wherein the lower alcohol and/or lower glycol concentration and pH are appropriate for the eluting of glycosylated prolactin being substantially free of non-glycosylated prolactin; and d. eluting the non-glycosylated prolactin from the chromatographic column with a sufficient quantity of a second eluting solution comprising:

i. at least one lower alcohol and/or lower glycol in concentration less than 50% per total volume; and ii. at least one salt, wherein the salt concentration, lower alcohol and/or lower glycol concentration and pH are appropriate for the eluting of non-glycosylated prolactin being substantially free of glycosylated prolactin.

12. A method according to claim 11, wherein the prolactin is human prolactin.

13. A method according to claim 11, wherein the lower alcohol is n-butanol.

14. A method according to claim 11, wherein the lower glycol is ethylene glycol.

15. A method according to claim 11, wherein the packing is a resin.

16. A method for separating glycosylated prolactin from non-glycosylated prolactin comprising:

a. equilibrating a solution containing glycosylated and non-glycosylated prolactin with an equilibrating solution containing at least one lower alcohol or lower glycol;

b. adding the equilibrated prolactin solution onto a chromatographic column containing a cationic or anionic packing for the ion exchange separation of glycosylated and non-glycosylated prolactin;

c. eluting the glycosylated prolactin from the chromatographic column with a sufficient quantity of a first eluting solution comprising:

i. at least one lower alcohol and/or lower glycol in concentration less than 50% per total volume; and ii. at least one salt, wherein the salt concentration, lower alcohol and/or lower glycol concentration and pH are appropriate for the eluting of glycosylated prolactin being substantially free of non-glycosylated prolactin; and d. eluting the non-glycosylated prolactin from the chromatographic column with a sufficient quantity of a second eluting solution containing at least one lower alcohol and/or lower glycol in concentration less than 50% per total volume, wherein the lower alcohol and/or lower glycol concentration and pH are appropriate for the eluting of non-glycosylated prolactin being substantially free of glycosylated prolactin.

17. A method according to claim 16, wherein the prolactin is human prolactin.

18. A method according to claim 16, wherein the lower alcohol is n-butanol.

19. A method according to claim 16, wherein the lower glycol is ethylene glycol.

20. A method according to claim 16, wherein the packing is a resin.

21. A method for separating glycosylated prolactin from non-glycosylated prolactin comprising:

a. equilibrating a solution containing glycosylated and non-glycosylated prolactin with an equilibrating solution containing at least one lower alcohol and/or lower glycol;

b. adding the equilibrated prolactin solution onto a chromatographic column containing a cationic or anionic packing for the ion exchange separation of glycosylated and non-glycosylated prolactin;

c. eluting the glycosylated prolactin from the chromatographic column with a sufficient quantity of a first eluting solution containing at least one lower alcohol and/or lower glycol in concentration less than 50% per total volume, wherein the lower alcohol and/or lower glycol concentration and pH are appropriate for the eluting of glycosylated prolactin being substantially free of non-glycosylated prolactin; and d. eluting the non-glycosylated prolactin from the chromatographic column with a sufficient quantity of a second eluting solution containing at least one lower alcohol and/or lower glycol in concentration less than 50% per total volume, wherein the lower alcohol and/or lower glycol concentration and pH are appropriate for the eluting of non-glycosylated prolactin being substantially free of glycosylated prolactin.

* * * * *